(12) United States Patent
Takarada et al.

(10) Patent No.: US 11,478,495 B2
(45) Date of Patent: Oct. 25, 2022

(54) AMPK ACTIVATING AGENT

(71) Applicant: ORYZA OIL & FAT CHEMICAL CO., LTD., Aichi (JP)

(72) Inventors: Toru Takarada, Aichi (JP); Hiroshi Shimoda, Aichi (JP); Hiromichi Murai, Aichi (JP)

(73) Assignee: ORYZA OIL & FAT CHEMICAL CO., LTD., Aichi (JP)

( * ) Notice: Subject to any disclaimer, the term of this patent is extended or adjusted under 35 U.S.C. 154(b) by 0 days.

(21) Appl. No.: 16/759,818

(22) PCT Filed: Nov. 10, 2019

(86) PCT No.: PCT/JP2019/044034
§ 371 (c)(1),
(2) Date: Apr. 28, 2020

(87) PCT Pub. No.: WO2020/110674
PCT Pub. Date: Jun. 4, 2020

(65) Prior Publication Data
US 2021/0268011 A1 Sep. 2, 2021

(30) Foreign Application Priority Data
Nov. 26, 2018 (JP) .............................. JP2018-220567

(51) Int. Cl.
*A61K 31/7048* (2006.01)
*A23L 33/105* (2016.01)
*A23L 2/52* (2006.01)
*A61K 8/60* (2006.01)
*A61K 36/82* (2006.01)

(52) U.S. Cl.
CPC ............ *A61K 31/7048* (2013.01); *A23L 2/52* (2013.01); *A23L 33/105* (2016.08); *A61K 8/60* (2013.01); *A61K 36/82* (2013.01); *A61K 2236/333* (2013.01); *A61K 2236/51* (2013.01)

(58) Field of Classification Search
None
See application file for complete search history.

(56) References Cited

FOREIGN PATENT DOCUMENTS

JP 2007-082508 4/2007
JP 2016-175842 10/2016

OTHER PUBLICATIONS

Takashi et al., JP 2016175842 A, 2016, machine translation, Retrieved on Feb. 22, 2022 from http://worldwide.espacenet.com (Year: 2016).*
Suzuki, T., Pervin, M., Goto, S., Isemura, M., & Nakamura, Y. (2016). Beneficial effects of tea and the green tea catechin epigallocatechin-3-gallate on obesity. Molecules, 21(10), 1305. (Year: 2016).*
Shimoda, H. et al., "Purple tea and its extract . . . carnitine palmitoyltransferase expression", International Journal of Biomedical Science, Jun. 2015, vol. 11, No. 2, pp. 67-75.
T. Kadekaru et al., "Function as a beauty . . . on purple tea extract" Fragrance Journal, 2014, vol. 42, No. 1, pp. 44-48.
Egawa, T. et al., "Activation of 5' AMP-activated . . . exercise and phytochemicals", Journal of Physical Fitness and Sports Medicine, 2014, vol. 3, No. 1, pp. 55-64.
Steinberg, G. R. et al., "AMPK in Health and Disease" Physiol Rev., vol. 89, No. 3, pp. 1025-1078 (2009).
Mair, W. et al., "Lifespan extension induced . . . mediated by CRTC-1 and CREB" Nature, vol. 470, No. 7334, pp. 404-408 (2011).
Narkar, V. A. et al., "AMPK and PPARS Agonists Are Exercise Mimetics" Cell, vol. 134, No. 3, pp. 405-415 (2008).
Minokoshi, Y. et al., "Leptin stimulates fatty-acid . . . activated protein kinase," Nature, vol. 415, No. 6869, pp. 339-343 (2002).

* cited by examiner

*Primary Examiner* — Dale R Miller
(74) *Attorney, Agent, or Firm* — Clark & Brody LP

(57) ABSTRACT

An AMP-activated protein kinase (AMPK) activating agent comprises 1,2-di-O-galloyl-4,6-O—(S)-hexahydroxydiphenoyl-b-D-glucose ("GHG") as an active ingredient. The AMPK activating agent can be a GHG-containing composition wherein the GHG is an active ingredient of the composition. The GHG-containing composition can be derived from Kenyan purple tea, whose scientific name is *Camellia sinensis*, variety name: TRFK306. An effective amount of the GHG can be administered to a cell to activate the AMPK. Drinks, foods, and cosmetics can have the GHG as an active ingredient.

4 Claims, 1 Drawing Sheet

HPLC of the purple tea extract

AMPK ACTIVATING AGENT

TECHNICAL FIELD

This invention relates to an AMPK activating agent, especially to a substitute composition for exercising; to an obesity-prevention composition and/or obesity-amelioration composition; to a cell-activating composition; to a skin care composition; or to food and drink having an AMPK activating agent.

TECHNICAL BACKGROUND

AMPK (i.e. AMP-activated protein kinase) is a serine/threonine kinase that is widely expressed in most eukaryotic cells of yeast, from plants to mammals, and plays an important role in regulating cellular-energy metabolism.

AMPK is activated in response to an increase in the ratio between intracellular AMP and ATP, with a decrease in the intracellular ATP level. Then, a downstream ground substance of the energy-production route is phosphorylated to enhance fatty-acid oxidation and sugar uptake, thus restoring the ATP level. AMPK is a trimer formed by an a sub-unit having a catalytic effect and by a ß sub-unit and a γ sub-unit both having a regulatory effect. The a sub-unit has an AMPKα1 and a subtype of AMPKα2. Both types form a complex similar to the ß sub-unit and γ sub-unit.

So far, it is known that a substance for activating the AMPK is effective in averting loss of muscle strength and in increasing such strength (Non-patent document 1). It is known too that activation of the AMPK delays the aging of nematode (*C. elegans*), which is importantly recognized as a therapeutic target for pathological change caused by aging in mammals (Non-patent document 2). It has been recently known that the amount of fat in a mutant mouse, which fat is less active in both AMPKα1 and AMPKα2, is not significantly reduced even if some amount of exercise is given to such mutant mouse but of which such exercise is enough for a normal mouse in reducing fat (Patent Document 1). It is suggested then that a decrease in the AMPK function is a risk factor in causing glucose intolerance, hyperlipidemia, high-blood pressure, coronary artery disorder and arteriosclerotic disease.

One of the more significant results of the research of AMPK activation is that such research has verified that AMPK activation is directly linked to the formation of skeletal muscles. Dr. Ronald Evans et. al. orally administered the AMPK agonist, that is, 5-aminoimidazole-4-carboxamide (AICAR) to mice for four weeks. They then verified that although no exercise had been imposed, the running endurance of the mice increased by 44% (Non-patent Document 3). Their report says that the ratio of subcutaneous fat to the body weight of the AICAR group decreased compared to that of the mice of the control group, and that oxygen intake improved in a state of no change in body weight.

Therefore, it was proven that the medical agent for activating the AMPK is useful in improving health by increasing muscle mass and muscle strength.

It was found in recent research that the AMPK is activated by AICAR or other substances e.g. metformin or the like as an anti-diabetes agent (Non-patent Document 4). However, these synthetic-chemical agents cause side effects, and such agents are difficult to use in foods. Thus, it is expected that an AMPK activator should be used that has fewer side effects and which would be more secure and excellent in processing various applications.

PRIOR ART

Patent Document

Patent Document 1: Japanese published unexamined application No. 2007-082508.
Non-Patent Document 1: Steinberg, G. R. et al., "Physiol Rev.," Vol. 89, No. 3, pp. 1025-78 (2009).
Non-Patent Document 2: Mair, W. et al., "Nature," Vol. 470, No. 7334, pp. 404-8 (2011).
Non-Patent Document 3: Narkar, V. A. et al., "Cell," Vol. 134, No. 3, pp. 405-15 (2008)
Non-Patent Document 4: Minokoshi, Y. et al., "Nature," Vol. 415, No. 6869, pp. 339-43 (2002).

DISCLOSURE OF THE INVENTION

Problems to be Resolved by the Invention

Under such conditions, the Inventors of this invention identified purple tea and its original substance, that is, 1,2-di-O-galloyl-4,6-O—(S)-hexahydroxydiphenoyl-b-D-glucose (GHG), as having an AMPK activating effect, thus achieving this invention. In other words, this invention is to provide a new AMPK activating agent.

Means for Solving the Problems

The technical features of this invention for solving the referenced problems above are as follows.
1. An AMPK activating agent comprising 1,2-di-O-galloyl-4,6-O—(S)-hexahydroxydiphenoyl-b-D-glucose (hereinafter referred to as "GHG") as an active ingredient.
2. An AMPK activating agent comprising a GHG-containing composition in which the GHG itself is an active ingredient.
3. An AMPK activating agent comprising a GHG-containing composition derived from Kenyan purple tea (scientific name: *Camellia sinensis*, variety name: TRFK306).
4. A method for activating an AMPK in a cell, characterized in that an effective amount of GHG is administered to the cell.
5. A method for activating an AMPK in a cell, characterized in comprising the following steps A to C:
A. The step of extracting GHG in the solvent by immersing Kenyan purple tea (scientific name: *Camellia sinensis*, variety name: TRFK306) in a polar solvent,
B. The step of concentrating the extract obtained in step A to obtain a GHG-containing composition;
C. The step of administering an effective amount of a GHG-containing composition to the cells.
6. A method for activating an AMPK in a cell, characterized in comprising the following steps A to C:
A. The step of extracting GHG in the solvent by immersing a leaf of Kenyan purple tea (scientific name: *Camellia sinensis*, variety name: TRFK306) in hydrous ethanol,
B. The step of concentrating the extract obtained in step A to obtain a GHG-containing composition;
C. The step of administering an effective amount of a GHG-containing composition to the cells.
7. A composition of drinks and foods for activating an AMPK, comprising GHG as an active ingredient.
8. A composition of cosmetics for activating an AMPK, comprising GHG as an active ingredient.

MODES FOR CARRYING OUT THE INVENTION

Figure 1:
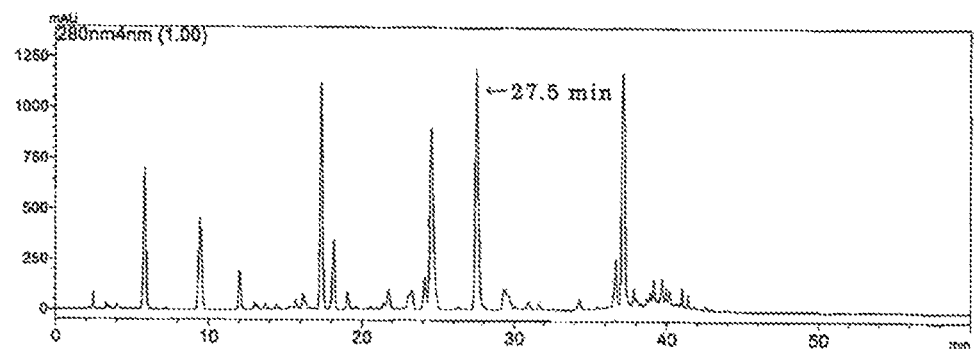
FIG. 1 is an HPLC chromatogram of Kenyan purple-tea extract (purple tea extract) as an embodiment of this invention.

The details of the invention are described below.

The AMPK activating agent of this invention is characterized in that 1,2-di-O-galloyl-4,6-O—(S)-hexahydroxydiphenoyl-b-D-glucose (hereinafter referred to as GHG) is the active substance.

Chemical Formula 1

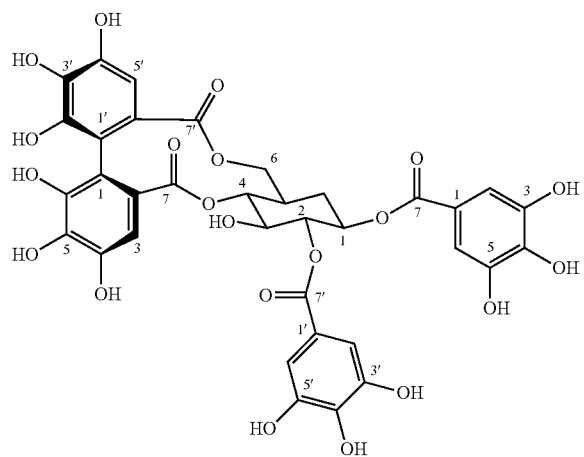

Chemical Formula (1)

The AMPK activating agent of this invention may be a single GHG or a composition containing GHG as an active ingredient. As for this composition having GHG, it is preferable to use Kenyan purple tea (scientific name: *Camellia sinensis*; variety name: TRFK306). The above composition having GHG is derived from Kenyan purple tea, which has GHG of 3 to 99 percent by mass. The form of such GHG can be liquid, solid, semi-solid or gel or the like. The solid-content-equivalent quantity of such GHG should be 3 to 99 percent by mass. However, in the case that such GHG-content extract is used as an ingredient in foods and drinks and cosmetics, it should be 3 to 30 percent by mass to increase its productivity, or, preferably, 3 to 10 percent by mass. The composition having GHG of 3 to 10 percent by mass can be derived effectively by the following production method.

The Kenyan purple tea used in deriving the composition having GHG is a crossbred-tea plant (scientific name: *Thea sinensis*) that was developed by the Kenyan government. Its variety name is TRFK306. The leaf of Kenyan purple tea has anthocyanin, is purple, and is also called just, "purple tea." A purple tea other than TRFK306 is Sun Rogue or the like, which was developed by an agricultural research group called the National Agriculture and Food Research Organization. Kenyan purple tea, however, has the specific active substance of GHG in high concentration that does not exist in other purple teas.

The part of Kenyan purple tea used in deriving the composition having GHG of this invention is not specified. The leaf, stem, root, flower or seed or the like can be used. The leaf is preferable, since it is possible to get from it a high level of GHG.

The composition having GHG of this invention preferably can be derived by crushing e.g. the fresh or dried leaves of Kenyan purple tea (hereinafter called purple tea) and then deriving the composition having GHG from such fresh or dried leaves by using a polar solvent (with water). Hereinafter the same shall apply. However, the GHG-content extract can be more efficiently extracted by chemically treating the purple-tea leaves with an acid or alkaline decomposition or enzyme decomposition or the like.

Specifically, by using the following method, the composition having the GHG extract can be derived. Firstly, chemically treat with an acid or alkaline decomposition or enzyme decomposition or the like the fresh or dried purple-tea leaves.

Secondly, add the polar solvent to the purple-tea leaves. Then, shake or reflux them by heating them to extract the GHG into the solvent.

At this time, not only a polar solvent can be used but also water, alcohol or ketone. Also, a mixture of one or more of these solvents can be used. It is preferable to use either aqueous alcohol or aqueous ketone.

An aqueous solvent such as ethanol, methanol, propanol or the like can be used as an aqueous-alcoholic solvent. An aqueous solvent such as acetone, methylethylketone, diethyl ketone, chloroacetone or the like can be used as an aqueous-ketonic solvent. An aqueous-acetone solvent is preferred.

If using aqueous ethanol, the ratio of water should be 1 to 99.9 percent by mass, preferably 30 to 99 percent by mass, more preferably 40 to 80 percent by mass, most preferably 40 to 60 percent by mass. If using aqueous acetone, the amount of acetone preferably should be 20 to 99.9 percent by mass, since the GHG can be efficiently extracted within the above range. For the sake of simplicity, an ethanol of 80 percent by mass, with water of 20 percent by mass, should be signified as "80 percent hydrous ethanol."

In making the composition having GHG of this invention, heating and refluxing can be done by the well-known method of using aqueous-alcoholic solvent or aqueous-ketonic solvent. The heating temperature should be 30 to 95 degrees Celsius, preferably 30 to 50 degrees Celsius. The refluxing time should be from one to four hours.

In the process of making the composition having GHG of this invention, shaking, stirring or the like can be done accordingly as necessary.

In the process of making the composition having GHG of this invention, it is better to vacuum and distil the solvent after the GHG extract has been derived. This process forms an element of the extract without having to use an organic solvent. Also, this process can be applied to a food ingredient to be mixed with foods such as functional food, healthy food or the like, and to drinks, thus making it possible to meet safety standards or the like.

In the process of making the composition having GHG of this invention, it is possible to extract such GHG in stages by using several different solvents, thus making it possible to derive such GHG-content extract in a high concentration.

Specifically, add the purple-tea leaves either to the aqueous-alcoholic solvent or aqueous-ketonic solvent. Then, shake such solvent, or heat and reflux it to extract the GHG into the solvent, thus deriving the first extract. Next, by centrifugal-separation or the like, separate the extracted GHG from the residue not collected as GHG-content extract, and then add the other not-chosen-before (either aqueous-alcoholic or aqueous-ketonic) solvent to such residue and shake it or heat and reflux it to extract (any remaining) GHG into that solvent, thus deriving the second extract. Then, mix the first extract with the second extract. Needless to say, the second extract alone can be used as the purple-tea-leaf extract (GHG-content extract).

As the above extractions use several solvents in stages, it is thought that the purple-tea leaves that have gone through the process of the first extraction by using the aqueous-alcoholic solvent or aqueous-ketonic solvent would change, so that the feature i.e. the physical property of the purple-tea leaves would become suitable for the extraction. Therefore, it can be expected that the process of the second extraction makes it possible to improve the efficiency of extraction, even if a solvent other than an aqueous-alcoholic solvent or aqueous-ketonic solvent is used.

The extracted liquid derived by the above method can be directly concentrated into the composition having the GHG. Also, such liquid can be freeze-dried or spray-dried into a powder, thus making a powdery composition having the GHG. However, such a GHG-content extract is not limited to being just in that condition. Insoluble matter within the extract can be removed accordingly by filtering such extract or the like, or such insoluble matter can be crushed into microscopic particles.

As a method for deriving the GHG of this invention, it is preferable to fractionate and distillate the composition having the GHG that was derived by the above process based on the index that is the already known GHG by using an ion-exchange process, a size-exclusion chromatography process, a High-performance Liquid Chromatography (HPLC) process, a gel-filtration process, or a membrane-separation process or the like. Of course, it is possible to extract, derive and distillate the GHG from a material other than Kenyan purple tea. Also, it is possible accordingly to apply an organic-synthetic method.

The AMPK activating agent of this invention can be shaped into a drug or quasi-drugs such as tablets, granules, powdered medicines, liquids, powders, capsules, jellies or the like by adding base materials and carriers to the GHG or to the composition having GHG as the active ingredient. Also, the GHG or composition having GHG as the active ingredient of this invention can be used as the element in various foods, drinks and cosmetics. These components mean materials obtained technically by mixing the ingredients appropriate for various uses.

The examples of this invention regarding foods and drinks include e.g. edible oils (salad oils), confectionary (chewing gums, candies, caramels, chocolates, cookies, snacks, jellies, gummies, tablet-shaped sweets or the like), noodles (Japanese buckwheat noodles called Soba, Japanese wheat noodles called Udon, Japanese noodles called Ramen or the like), dairy food (milk, ice cream, yogurt, or the like), seasoning (fermented rice, barley, soybean paste or the like called Miso, soy sauce called Shoyu, or the like), soups, drinks (juice, coffee, black tea, green tea, carbonated drink, sports supplement drinks or the like) including general foods and healthy foods (tablet type, capsule type or the like) and nutritional supplements (nutritious supplement drink or the like). The GHG or composition having such GHG of this invention can be added accordingly to the above foods and drinks.

According to the type of food and drink elements, the following ingredients can be added: glucose, fructose, sucrose, maltose, sorbitol, stevioside, corn syrup, lactose, citric acid, tartaric acid, malic acid, succinic acid, lactic acid, L-ascorbic acid, dl-α-tocopherol, sodium erythorbate, glycerin, propylene glycol, glycerin fatty-acid ester, polyglycerol fatty-acid ester, sucrose fatty-acid ester, sorbitan fatty-acid ester, propylene glycol fatty-acid ester, Gum arabic, carrageenan, casein, gelatin, pectin, agar-agar (gelatin made from seaweed), the vitamin B family, nicotinic-acid amide, pantothenate acid calcium, amino acids, calcium salts, pigment, aroma chemicals, preservatives or the like.

Furthermore, of the food composition and beverage composition with a health maintenance function, it is possible to blend the agents such as other antioxidants and health food materials, e.g. antioxidants, reduced ascorbic acid (vitamin C), vitamin E, reduced glutatin, tocotrienol, vitamin A derivative, lycopene, beta-cryptoxanthin, astaxanthin, zeaxanthin, fucoxanthin, uric acid, ubiquinone, Coenzyme Q10, folic acid, garlic extract, alicine, sezamine, lignans, catechin, isoflavone, chalcon, tannins, flavonoids, coumarin, isokmarins, blueberry extract, albutin, tannin, anthocyanins, apple polyphenol, grape seed extract, elladic acid, kojic acid, surge extract, V. (vitamin) A, V.B1, V.B2, V.B6, V.B12, V.C, V.D, V.E, V.P, choline, niacin, pantothenic acid, calcium folic acid, EPA, oligosaccharides, dietary fiber, squalene, soybean lecithin, taurine, donaliela, protein, octacosanol, DHA, egg yolk lecithin, linoleic acid, lactoferrin, magnesium, zinc, chromium, selenium, potassium, heme iron, oyster meat extract, chitosan, chitin oligosaccharide, collagen, chondroitin, turmeric, sweetroot, *Lycium* chinese fruit, cinnamon cassia, hawthorn, ginger, bracket fungus, *Corbicula* extract, chinese soft-shell turtle, plantain, chamomile, dandelion, *hibiscus*, honey, boren, royal jelly, lime, lavender, rosehip, rosemary, sage, bifidobacteria, facaris, *Bacillus coagulans* SANK 70258, wheat germ oil, sesame oil, *perilla* oil, soybean oil, medium chain fatty acids, *agaricus, ginkgo* leaf extract, turmeric, chondroitin, brown rice germ extract, lychee, onion, DHA, EPA, DPA, Tencha tea, *Ophiocordyceps sinensis*, garlic, wasp larva, papaya, puerh tea, propolis, Acer maximowiczianum, *Hericium erinaceum*, Royal jelly, saw palmetto, hyaluronic acid, collagen, gaba, harp seal oil, shark cartilage, glucosamine, lecithin, phosphatidylserine, *Panax notoginseng*, mulberry leaves, soybean extract, *echinacea, Acanthopanax senticosus* Harms, barley extract, olive leaf, olive fruit, gymnema, *Lagerstroemia speciosa*, salacia, garcinia, chitosan, St. John's wort, Chinese date, carrot, passion flower, broccoli, placenta, adlay, grape seed, peanut testa, bilberry, black cohosh, milk thistle (*Silybum marianum*), laurel, sage, rosemary, *Apocynum venetum*, black vinegar, bitter gourd, maca, safflower, flax, oolong tea, flower thorn, caffeine, capsaicin, xylooligosaccharide, glucosamine, buckwheat, citrus, dietary fiber, protein, prune, spirulina, barley young leaf, nucleic acid, yeast, shiitake mushroom, plum meat, amino acid, deep-sea shark extract, noni, oyster meat, Chinese softshell turtle (*terrapin*), champignon, plantain, acerola, pineapple, banana, peach, apricot, melon, strawberry, raspberry, orange, fucoidan, *Fomes yucatensis*, cranberry, chondroitin sulfate, zinc, iron, ceramide, silk peptides, glycine, niacin, chastetree, ceramide, L-cysteine, L-carnitine, red wine leaves, millet, horsetail, biotin, centela asiatica, *Lonicera caerulea L. pycnogenol*, Japanese butterbur, rhubarb, clove, rosemary, catechin, puerh tea, citric acid, beer yeast, melilot, black ginger, ginger, *zedoaria*, nattokinase, monascuc, tocotrienol, lactoferrin, cinnamon, tartary buckwheat, cocoa, yuzu (Japanese citrus) seed extract, *perilla* fruit extract, lychee seed extract, evening primrose extract, black rice extract, alpha-lipoic acid, gaba, green coffee bean extract, Japanese butterbur extract, kiwi seed extract, Unshu citrus extract, red ginger extract, astaxanthin As a more specific method, spray-dry or freeze-dry the active ingredient of this invention i.e. the GHG or the composition having GHG. Especially, in the case of the GHG-content extract, spray-dry or freeze-dry it with dextrin powder, thus making such extract into a powder, a granule, a tablet or a liquid to mix it easily with foods (instant food or the like). Also, it is possible accordingly to mix such extract with a binder such as gum Arabic or the like to make it into a powder or a granule, thus making it possible in adding it to solid food.

In the case that the AMPK activating agent of this invention is formed into a pharmaceutical (including pharmaceuticals and quasi-drugs medicines), the active ingredients (GHG or the composition having GHG) of this invention can be aptly mixed with raw materials to form the pharmaceuticals. Such pharmaceuticals can be used for humans and other organisms (mammalians or the like). The raw materials to be mixed with the above pharmaceuticals include e.g. vehicles (glucose, lactose, sucrose, sodium chloride, starch, calcium carbonate, kaolin, crystalline cellulose, cacao oil, hydrogenated vegetable oil, talc or the like), binders (distilled water, normal saline solution, ethanolic solution, simple syrup, glucose solution, starch solution, gelatin solution, carboxymethyl cellulose, potassium phosphate, polyvinyl pyrrolidone, or the like), disintegrating agent (sodium alginate, agar-agar, sodium-hydrogen carbonate, calcium carbonate, sodium-lauryl sulphate, monoglyceride stearate, starch, lactose, gum arabic powder, gelatin, ethanol, or the like), disintegration-suppressive agent (sucrose, stearin, cacao oil, hydrogenated oil, or the like), absorption promoters (quaternary-ammonium base, sodium lauryl sulphate, or the like), adsorbents (glycerin, starch, lactose, kaolin, bentonite, silica acid, or the like), lubricant agents (purified talc, stearate, polyethylene glycol, or the like) or the like.

As a method for administering the above medicines, it is possible to administer them orally in the form of tablets, pills, soft or hard capsules, subtle granules, powders or granules or the like. Water-soluble preparations can either be orally administered in liquid form or be parenterally administered after having dispersed them into a solubilizer such as ethanol, water or the like, or into the different forms of a medical skin-patch, or into a lotion, an ointment, a tincture or a cream or the like. Also, the water-soluble prepared medicines can simply be used or mixed with a dispersant, a suspension agent or a stabilizer or the like, thus making it possible to use such preparations (prepared medicines) in the form of a medical skin-patch, a lotion, an ointment, a tincture or a cream or the like.

The applied dose can be adjusted according to the method of administration, to the condition of the disease, or to the age of the patient or the like. Adults normally can take approx. 5.0 to 200 mg of an active ingredient per day; children can take 0.5 to 100 mg per day.

The blending ratio of the active ingredient (i.e. the GHG or the composition having GHG) of this invention can be adjusted according to the way in which the medicine is to be administered. When such active ingredient is to be orally or mucosally administered, the applied dose should preferably be about 0.01 to 10.0 wt %. When it is to be parenterally administered, the dose should preferably be 0.01 to 20 wt %. The dose varies depending on the condition of the patient, so that a dose less than the above amount may be sufficient, or a greater amount may sometimes be needed. Medicinal elements possibly contain other ingredients, such as the already-known ingredients regularly used in the pharmaceutical field, and those ingredients necessary to make the active ingredient into any suitable form to be orally applied, including e.g. lactose, starch, hydroxypropylcellulose, kaolin, talc or calcium carbonate or the like.

Forms of the cosmetic-elements of this invention include e.g. emulsions, soaps, facial cleansers, bath agents, creams, skin lotions, colognes, shaving creams, shaving lotion, beauty oils, sunscreen lotions, face powders, foundations, perfumes, facial masks, nail creams, nail enamels, nail-polish removers, eyebrow pencils, blushers, eye creams, eye shadows, mascaras, eye liners, lip sticks, lip creams, shampoos, hair conditioners, hair colors, dispersion liquids, cleansing preparations or the like.

Within the useful range of the active ingredients (GHG or the composition having GHG) of this invention, the above items for skin care can be mixed with the ingredients of cosmetics or of quasi-drugs or the like, including e.g. oil, higher alcohol, fatty acids, ultraviolet absorbers, powders, pigments, surface-active agents, polyhydric alcohol and sugar, polymers, biologically active ingredients, solvents, antioxidants, aroma chemicals and antiseptics.

However, such ingredients usable in the present invention are not limited to these examples.

(1) Specific Examples of Oil

Ester-Type Oil Phase Ingredient:

Glyceryl tri-2-ethylhexanoate, cetyl 2-ethylhexanoate, isopropyl myristate, butyl myristate, isopropyl palmitate, ethyl stearate, octyl palmitate, isocetyl isostearate, butyl stearate, butyl myristate, ethyl linoleate, isopropyl linoleate, ethyl oleate, isocetyl myristate, isostearyl myristate, isostearyl palmitate, octyl dodecyl myristate, isocetyl isostearate, diethyl sebacate, diisopropyl adipate, isoaralkyl neopentanoate, glyceryl tri (caprylate/caprate), trimethylolpropane tri-2-ethylhexanoate, trimethylolpropane triisostearate, pentaerythritol tetra-2-ethylhexanoate, cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl myristate, isostearyl myristate, isocetyl palmitate, isostearyl palmitate, octyl stearate, isocetyl stearate, isodecyl oleate, octyldodecyl oleate, octyldodecyl linoleate, isopropyl isostearate, cetostearyl 2-ethylhexanoate, stearyl 2-ethylhexanoate, hexyl isostearate, ethylene glycol dioctanoate, ethylene glycol dioleate, propylene glycol dicaprate, propylene glycol di caprylate/dicaprate), propylene glycol dicaprylate, neopentyl glycol dicaprate, neopentyl glycol dioctanoate, glyceryl tricaprylate, glyceryl triundecylate, glyceryl triisopalmitate, glyceryl triisostearate, octyldodecyl neopentanoate, isostearyl octanoate, octyl isononanoate, hexyldecyl neodecanoate, octyldodecyl neodecanoate, isocetyl isostearate, isostearyl isostearate, octyldecyl isostearate, polyglyceryl oleate, polyglycerol Glycerin isostearate, dipropyl carbonate, dialkyl carbonate (C12-18), triisocetyl citrate, triisoaralkyl citrate, triisooctyl citrate, lauryl lactate, myristyl lactate, cetyl lactate, octyldecyl lactate, triethyl citrate, acetyltriethyl citrate, acetyltributyl citrate, trioctyl citrate, diisostearyl malate, 2-ethylhexyl hydroxystearate, di(2-ethylhexyl) succinate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoyl hydroxystearate, stearyl 12-stearoyl hydroxystearate, isostearyl 12-stearoyl hydroxystearate, or the like.

Hydrocarbon-Type Oil Phase Ingredient:

Squalene, liquid paraffin, α-olefin oligomer, isoparaffin, ceresin, paraffin, liquid isoparaffin, polybutene, microcrystalline wax, Vaseline or the like.

Animal and Plant Oil, Hardened Oil Thereof, and Wax of Natural Origin:

Animal oils and hardened oils thereof, such as beef tallow, hardened beef tallow, lard, hardened lard, horse oil, hardened horse oil, mink oil, orange roughy oil, fish oil, hardened fish oil, egg yolk oil or the like; plant oils and hardened oils thereof such as avocado oil, almond oil, olive oil, cacao oil, kiwifruit seed oil, apricot kernel oil, kukui nut oil, sesame oil, wheat germ oil, rice germ oil, rice bran oil, safflower oil, shea butter, soybean oil, evening primrose oil, perilla oil, tea seed oil, tsubaki oil (Camellia japonica oil), corn oil, rapeseed oil, hardened rapeseed oil, palm kernel oil, hardened palm kernel oil, palm oil, hardened palm oil, peanut oil, hardened peanut oil, castor oil, hydrogenated castor oil, sunflower oil, grape seed oil, jojoba oil, hardened jojoba oil, macadamia nut oil, meadowfoam seed oil, cottonseed oil, hardened cottonseed oil, coconut oil, hardened coconut oil, or the like; and waxes such as beeswax, high acid number beeswax, lanolin, reduced lanolin, hardened lanolin, liquid lanolin, carnauba wax and montan wax, or the like.

Silicone-Type Oil Phase Ingredient:

Dimethylpolysiloxane, methylphenyl-polysiloxane, methylcyclopolysiloxane, octamethylpolysiloxane, decamethylpolysiloxane, dodecamethylcyclosiloxane, methylhydrogenpolysiloxane, polyether-modified organopolysiloxane, dimethylsiloxane and methylcetyloxysiloxane Polymer, dimethylsiloxane/methylstearoxysiloxane copolymer, alkyl-modified organopolysiloxane, terminal-modified organopolysiloxane, amino-modified silicone oil, amino-modified organopolysiloxane, dimethiconol, silicone gel, acrylic silicone, trimethylsiloxysilicic acid, Silicone RTV rubber, or the like.

Fluorine-Type Oil Phase Ingredient:

Perfluoropolyether, fluorine-modified organopolysiloxane, pitch fluoride, fluorocarbon, fluoroalcohol, fluoroalkyl/polyoxyalkylene co-modified organopolysiloxane, or the like.

(2) Specific Examples of Higher Alcohol:

Lauryl alcohol, myristyl alcohol, cetyl alcohol, stearyl alcohol, isostearyl alcohol, oleyl alcohol, behenyl alcohol, 2-ethylhexanol, hexadecyl alcohol and octyl dodecanol or the like.

(3) Specific Examples of Fatty Acids:

Caprylic acid, capric acid, undecylenic acid, lauric acid, myristic acid, palmitic acid, palmitoleic acid, stearic acid, isostearic acid, oleic acid, linoleic acid, linolenic acid, arachic acid, arachidonic acid, behenic acid, erucic acid, 2-ethylhexanoic acid or the like.

(4) Specific Examples of Ultraviolet Absorber:

Para-aminobenzoic acid, amyl para-aminobenzoate, ethyldihydroxypropyl para-aminobenzoate, glyceryl para-aminobenzoate, ethyl para-aminobenzoate, octyl para-aminobenzoate, octyldimethyl para-aminobenzoate, ethylene glycol salicylate, octyl salicylate, triethanolamine salicylate, phenyl salicylate, butylphenyl salicylate, benzyl salicylate, homomenthyl salicylate, benzyl cinnamate, octyl para-methoxycinnamate, 2-ethylhexyl para-methoxycinnamate, glyceryl mono-2-ethyl hexanoate di-para-methoxycinnamate, isopropyl para-methoxycinnamate, diethanolamine para-methoxyhydrocinnamate, diisopropyl diisopropylcinnamic acid ester mixture, urocanic acid, ethyl urocanate, hydroxymethoxybenzophenone, hydroxymethoxybenzophenone sulfonic acid and a salt thereof, dihydroxymethoxybenzophenone, sodium dihydroxymethoxybenzophenonedisulfonate, dihydroxybenzophenone, dihydroxydimethoxybenzophenone, hydroxyoctoxybenzophenone, tetrahydroxybenzophenone, butylmethoxydibenzoylmethane, 2,4, 6-trianilino-p-(carbo-2-ethylhexyl-1-oxy)-1,3,5-triazine, 2-(2-hydroxy-5-methylphenyl) benzotriazole, methyl-O-aminobenzoate, 2-ethylhexyl-2-cyano-3,3-diphenylacrylate, phenylbenzimidazole sulfuric acid, 3-(4-methylbenzylidene) camphor, isopropyldibenzoylmethane, 4-(3, 4-dimethoxyphenylmethylene)-2, 5-doxy-1-imidazolidinepropionate, and polymer derivatives and silane derivatives thereof, or the like.

(5) Specific Examples of Powder and Pigment:

Pigments such as Food Red 104, Food Red 201, Food Yellow 4, Food Blue 1 and Food Black 401; lake pigments such as Food Yellow 4 AL lake and Food Yellow 203 BA lake; polymers such as nylon powder, silk powder, urethane powder, Teflon® powder, silicone powder, polymethyl methacrylate powder, cellulose powder, starch, silicone elastomer spherical powder and polyethylene powder; color pigments such as yellow iron oxide, red iron oxide, black iron oxide, chromium oxide, carbon black, ultramarine and iron blue; white pigments such as zinc oxide, titanium oxide and cerium oxide; extender pigments such as talc, mica, sericite, kaolin and plate barium sulfate; pearl pigments such as mica titanium; metal salts such as barium sulfate, calcium carbonate, magnesium carbonate, aluminum silicate and magnesium silicate; inorganic powders such as silica and alumina; metal soaps such as aluminum stearate, magnesium stearate, zinc palmitate, zinc myristate, magnesium myristate, zinc laurate and zinc undecylenate; bentonite; smectite; and boron nitride. The shape (e.g., sphere, bar, needle, plate, amorphous, scale, spindle) and the particle size of these powders are not particularly limited. These powders may or may not be previously surface-treated by a conventionally known surface treatment such as fluorine compound treatment, silicone treatment, silicone resin treatment, pendant treatment, saline coupling agent treatment, titanium coupling agent treatment, lubricant treatment, N-acylated lysine treatment, polyacrylic acid treatment, metal soap treatment, amino acid treatment, lecithin treatment, inorganic compound treatment, plasma treatment and mechanochemical treatment.

(6) Specific examples of surfactants

Anionic Surfactant:

Fatty-acid soap, a-acyl sulfonate, alkyl sulfonate, alkylallyl sulfonate, alkylnaphthalene sulfonate, alkyl sulfate, POE alkyl ether sulfate, alkylamide sulfate, alkyl phosphate, POE alkyl phosphate, alkylamide phosphate, alkyloylalkyl taurine salt, N-acylamino acid salt, POE alkyl ether carbonate, alkyl sulfosuccinate, sodium alkylsulfoacetate, acylated hydrolyzed collagen peptide salt, perfluoroalkylphosphoric acid ester or the like.

Cationic Surfactant:

Alkyltrimethylammonium chloride, stearyltrimethylammonium chloride, stearyltrimethylammonium bromide, cetostearyltrimethylammonium chloride, distearyldimethylammonium chloride, stearyldimethylbenzylammonium chloride, behenyltrimethylammonium bromide, benzalkonium chloride, behenic acid amidopropyldimethyl hydroxypropylammonium chloride, diethylaminoethylamide stearate, dimethylaminoethylamide stearate, dimethylaminopropylamide stearate, lanolin derivative quaternary ammonium salt or the like.

Amphoteric Surfactant:

Carboxybetaine type, amidobetaine type, sulfobetaine type, hydroxysulfobetaine type, amidosulfobetaine type, phosphobetaine type, aminocarboxylate type, imidazoline derivative type, amidoamine type or the like.

Nonionic Surfactant:

Propylene glycol fatty-acid ester, glycerin fatty-acid ester, polyglycerin fatty-acid ester, sorbitan fatty-acid ester, POE sorbitan fatty-acid ester, POE sorbitol fatty-acid ester, POE glycerin fatty-acid ester, POE alkyl ether, POE fatty-acid ester, POE hydrogenated castor oil, POE castor oil, POE-POP copolymer, POE-POP alkyl ether, polyether-modified silicone lauric acid alkanolamide, alkylamine oxide, hydrogenated soybean phospholipid or the like.

Natural-Type Surfactant:

Lecithin, saponin, sugar-type surfactant or the like.

(7) Specific Examples of Polyhydric Alcohol and Sugar

Ethylene glycol, diethylene glycol, polyethylene glycol, propylene glycol, dipropylene glycol, polypropylene glycol, glycerin, diglycerin, polyglycerin, 3-methyl-1, 3-butanediol, 1,3-butylene glycol, sorbitol, mannitol, raffinose, erythritol, glucose, sucrose, fruit sugar, xylitol, lactose, maltose, maltitol, trehalose, alkylated trehalose, mixed isomerized sugar, sulfated trehalose, pullulan or the like. Chemically modified products thereof can also be used.

(8) Specific Examples of Polymer Compound

Anionic polymer compounds such as acrylic acid ester/methacrylic acid ester copolymer (PLUS-SIZE, produced by Sogokagaku K. K.), vinyl acetate/crotonic acid copolymer (Resin 28-1310, produced by NSC), vinyl acetate/crotonic acid/vinyl neodecanate copolymer (28-2930, produced by NSC), methyl vinyl ether maleic acid half ester (GANTREZ ES, produced by ISP), T-butyl acrylate/ethyl acrylate/methacrylic acid copolymer (RUBIMER, produced by BASF), vinylpyrrolidone/vinyl acetate/vinyl propionate copolymer (RUBISCOL VAP, produced by BASF), vinyl acetate/crotonic acid copolymer (RUBISET CA, produced by BASF), vinyl acetate/crotonic acid/vinylpyrrolidone copolymer (RUBISET CAP, produced by BASF), vinylpyrrolidone/acrylate copolymer (RUBIFLEX, produced by BASF), acrylate/acrylamide copolymer (ULTRAHOLD, produced by BASF), vinyl acetate/butyl maleate-isobornyl acrylate copolymer (ADVANTAGE, produced by ISP), carboxy vinyl polymer (CARBOPOL, produced by BF Goodrich) and acrylic acid-alkyl methacrylate copolymer (PAMUREN, produced by BF Goodrich); amphoteric polymer compounds such as acetic acid amphoteric compound of dialkylaminoethyl methacrylate polymer (YUKAFORMER, produced by Mitsubishi Chemical) and octylacrylamide acrylate/hydroxypropyl acrylate/butylaminoethyl methacrylate copolymer (AMPHOMER, produced by NSC); cationic polymer compounds such as quaternized compound of vinylpyrrolidone/dimethylaminoethyl methacrylate (GAFQUAT, produced by ISP) and methyl vinyl imidazolium chloride/vinylpyrrolidone copolymer (RUBICOTE, produced by BASF); and nonionic polymer compounds such as polyvinylpyrrolidone/vinyl acetate copolymer (RUBISCOL VA, produced by BASF) and vinylpyrrolidone/dimethylaminoethyl methacrylate copolymer (COPOLYMER VC713, produced by ISP).

In addition, polymer compounds of natural origin, such as cellulose and derivatives thereof, calcium alginate, pullulan, agar, gelatin, tamarind seed polysaccharides, xanthane gum, carrageenan, high-methoxyl pectin, low-methoxyl pectin, guar gum, gum arabic, crystal cellulose, arabino galactan, karaya gum, tragacanth gum, alginic acid, albumin, casein, cardrun, gellan gum, dextran or the like, can also be suitably used.

(9) Specific Examples of Biologically Active Ingredients

The biologically active ingredient may include substances that are capable of imparting some biological activity to skin when such a substance is applied to the skin. Specific examples thereof may include: whitening ingredient, immunomodulator, age resistor, ultraviolet protection, slimming agent, skin tightening agent, antioxidant, hair restorer, hair growing agent, moisturizer, blood circulation accelerator, antibacterial agent, bactericide, desiccant, cooling agent, warming agent, vitamin compound, amino acid, wound healing accelerator, torpent, analgetic, cell activator and enzyme ingredient.

Suitable examples of the ingredient to be blended therefor may include: *angelica* extract, avocado extract, *hydrangea* extract, *althea* extract, *arnica* extract, aloe extract, apricot extract, apricot core extract, *ginkgo* extract, fennel extract, turmeric extract, oolong tea extract, rose fruit extract, *echinacea* leaf extract, *scutellaria* root extract, *phellodendron* bark extract, goldthread extract, barley extract, *hypericum* extract, white nettle extract, watercress extract, orange extract, sea salt, seaweed extract, hydrolyzed elastin, hydrolyzed wheat powder, hydrolyzed silk, chamomile extract, carrot extract, *Artemisia capillaris* extract, *glycyrrhiza* extract, *Hibiscus sabdariffa* extract, *Pyracantha fortuneana* fruit extract, *cinchona* extract, cucumber extract, guanosine, *gardenia* extract, *Sasa albo-marginata* extract, *Sophora* root extract, walnut extract, grapefruit extract, *clematis* extract, *chlorella* extract, mulberry bark extract, gentian extract, black tea extract, yeast extract, burdock extract, fermented rice bran extract, rice germ oil, comfrey extract, collagen, cowberry extract, *Asiasarum* root extract, *Bupleurum falcatum* root extract, umbilical cord extract, *salvia* extract, *saponaria* extract, bamboo grass extract, *crataegus* extract, *zanthoxylum* fruit extract, shiitake mushroom extract, *Rehmannia* root extract, *lithospermum* root extract, *perilla* extract, linden extract, *filipendula* extract, peony root extract, *calamus* rhizome extract, birch extract, horsetail extract, ivy extract, hawthorn extract, *Sambucus nigra* extract, yarrow extract, peppermint extract, sage extract, mallow extract, *Cnidium* rhizome extract, *swertia* herb extract, soy extract, jujube extract, wild thyme extract, green tea extract, clove extract, cogon extract, citrus unshiu peel extract, *angelica* root extract, calendula extract, peach seed extract, bitter orange extract, *Houttuynia* extract, tomato extract, natto extract, *ginseng* extract, garlic extract, wild rose extract, *Hibiscus sabdariffa* flower extract, *ophiopogon* tuber extract, parsley extract, honey, witch hazel extract, pellitory extract, isodonis extract, *matricaria* extract, *loquat* extract, coltsfoot extract, butterbur scape extract, *Poria cocos* extract, butcher bloom extract, grape extract, propolis, luffa extract, safflower extract, peppermint extract, linden extract, peony extract, hop extract, pine extract, horse chestnut extract, skunk cabbage extract, *sapindaceae* extract, balm mint extract, peach extract, cornflower extract, *eucalyptus* extract, saxifrage extract, *coix* seed extract, mugwort extract, lavender extract, apple extract, lettuce extract, lemon extract, Chinese milk vetch extract, rose extract, rosemary extract, Roman chamomile extract, royal jelly extract or the like.

Other examples may include biopolymers such as deoxyribonucleic acid, mucopolysaccharide, sodium hyaluronate, sodium, elastin, chitin, chitosan and hydrolyzed eggshell membrane; moisture retentive ingredients such as amino acid, hydrolyzed peptide, sodium lactate, urea, sodium pyrrolidonecarboxylate, betaine, whey and trimethylglycine; oily ingredients such as sphingolipid, ceramide, phytosphingosine, cholesterol, cholesterol derivatives and phospholipid; anti-inflammatory such as E-aminocaproic acid, glycyrrhizic acid, -glycyrrhetic acid, lysozyme chloride, guaiazlene and hydrocortisone; vitamins such as vitamin A, vitamin B2, vitamin B6, vitamin D, vitamin E, calcium pantothenate, biotin and nicotinic acid amide; active ingredients such as allantoin, diisopropylamine dichloroacetate and 4-aminomethylcyclohexanecarboxylic acid; antioxidants such as tocopherol, carotenoid, flavonoid, tannin, lignin and saponin; cell activators such as a-hydroxy acid and hydroxy acid; blood circulation accelerators such as y-orizanol and vitamin E derivatives; wound healing agents such as retinol and retinol derivatives; whitening agents such as albumin, kojic acid, placenta extract, sulfur, ellagic acid, linoleic acid, tranexamic acid and glutathione; and hair growing agents such as cepharanthine, *glycyrrhiza* extract, *capsicum* tincture, hinokitiol, iodized garlic extract, pyridoxine hydrochloride, DL-a-tocopherol, DL-a-tocopheryl acetate, nicotinic acid, nicotinic acid derivatives, calcium pantothenate, D-pantothenyl alcohol, acetyl pantothenylethyl ether, biotin, allantoin, isopropylmethylphenol, estradiol, ethynyl estradiol, capronium chloride, benzalkonium chloride, diphenhydramine hydrochloride, Takanal, camphor, salicylic acid, vanillylamide nonylate, vanillylamide nonanoate, pyroctone olamine, glyceryl pentadecanoate, L-menthol, mononitroguaiacol, resorcinol, y-aminobutyric acid, benzethonium chloride, mexiletine hydrochloride, auxin, female hormone, cantharis tincture, cyclosporine, zinc pyrithione, hydrocortisone, minoxidil, polyoxyethylene sorbitan monostearate, peppermint oil and SASANISHIKI extract, placenta products, *Citrus junos* seed extract, blueberry extract, lingonberry extract, *Cistanche tubulosa* extract, black rice extract, green coffee bean extract, resveratrol extract, kiwifruit seed extract, strawberry seed extract, cherry extract, or the like.

(10) Examples of Antioxidants

Plant extracts having an antioxidant effect, such as Sodium bisulfite, sodium sulfite, erythorbic acid, sodium erythorbate, dilauryl thiodipropionate, tocopherol, tolylbiguanide, nordihydroguaiaretic acid, parahydroxyanisole, butylhydroxyanisole, dibutylhydroxytoluene, ascorbyl stearate, palmitic acid, Ascorbyl, octyl gallate, propyl gallate, carotenoid, flavonoid, tannin, lignan, saponin, apple extract and clove extract, or the like.

(11) Examples of Solvents

Purified water, ethanol, lower alcohol, ethers, LPG, fluorocarbon, N-methylpyrrolidone, fluoroalcohol, volatile linear silicone, next-generation fluorocarbon, or the like.

Example

Hereinafter, a specific example of this invention is described, which is just one of many examples of this invention, and the scope of this invention is not limited just to this example.

[Preparation of the Purple-Tea Extract (of the Composition Having GHG)]

50 grams of Kenyan purple-tea leaf is immersed in 500 mL of a 50% aqueous solution of ethanol and then stirred and heated and refluxed at 40 degrees Celsius for two hours until such solution becomes the extracted liquid. 400 mL of this extracted liquid is derived by suction-filtration. Such extracted liquid is then concentrated and dried into 16.6 grams of the purple-tea extract.

[Analysis of the Element of the Purple-Tea Extract]

The purple-tea extract was analyzed by using the HPLC method. It was verified that the amount of the peculiar element of Kenyan purple tea peaks at 27.5 min, of which amount ordinary tea plants such as green tea, oolong tea, black tea or the like do not have (See the arrow of FIG. 1).

Preparation of samples: 350 mg of the purple-tea extract (GHG-content extract) was dissolved in a 30% aqueous-solution of methanol, and the volume was fixed at 20 mL in the measuring flask. The solution was diluted and filtered twice and then analyzed by the HPLC.

The result of the HPLC analysis was as follows.
<Condition of the HPLC Analysis>
Flow rate: 0.7 mL/min
Mobile phase A: 0.3% TFA aqueous solution
Mobile phase B: Acetonitrile
Gradient: As shown in Table 1 below
Chromatography: SunFire C18, 4.6×150 mm (Waters) or equivalent
Chromatography temperature: 30 degrees Celsius
Sample injection volume: 10 μL
Detection wavelength: 280 nm

CHART 1

| Time (min) | Mobile phase B Concentration (%) |
|---|---|
| 0.0 | 5 |
| 4.0 | 5 |
| 4.5 | 10 |
| 27.0 | 15 |
| 47.0 | 55 |
| 48.0 | 90 |
| 50.0 | 90 |
| 51.0 | 5 |
| 60.0 | 5 |

The above peculiar elements were separated and purified, and then an NMR analysis was done. The result of the known element 1,2-di-O-galloyl-4,6-O—(S)-hexahydroxydiphenoyl-8-D-glucose (GHG) having been identified is shown below in Chart 2.

CHART 2

Chart 2. C-NMR Data of GHG of purple tea component

| Carbon No. | Purified component derived from purple tea | GHG literature value 1) |
|---|---|---|
| glucose | | |
| 1 | 94.4 | 94.4 |
| 2 | 74.6 | 74.7 |
| 3 | 74.1 | 74.1 |
| 4 | 73.1 | 73.1 |
| 5 | 73.8 | 73.8 |
| 6 | 64.1 | 64.1 |
| galloyl | | |
| 1 | 119.9 | 119.9 |
| 2, 6 | 110.6 | 110.6 |
| 3, 5 | 146.5 | 146.5 |
| 4 | 140.6 | 140.7 |
| 7 | 166.3 | 166.4 |
| 1' | 120.9 | 120.9 |
| 2', 6' | 110.4 | 110.5 |
| 3', 5' | 146.4 | 146.4 |
| 4' | 140.1 | 140.1 |
| 7' | 167.2 | 167.3 |
| HHDP | | |
| 1 | 116.9 | 116.9 |
| 2 | 126.2 | 126.9 |
| 3 | 108.6 | 108.7 |
| 4 | 145.9 | 145.9 |
| 5 | 137.7 | 137.7 |
| 6 | 144.9 | 144.9 |
| 7 | 169.4 | 169.4 |
| 1' | 116.6 | 116.6 |
| 2' | 126.5 | 126.5 |
| 3' | 108.4 | 108.5 |
| 4' | 145.8 | 145.8 |
| 5' | 137.4 | 137.4 |

CHART 2-continued

Chart 2. C-NMR Data of GHG of purple tea component

| Carbon No. | Purified component derived from purple tea | GHG literature value 1) |
|---|---|---|
| 6' | 144.8 | 144.8 |
| 7' | 169.8 | 169.9 |

1) Chem. Pharm. Bull. 57(11) 1284-1288 (2009)

The GHG-refined element is set as the standard substance of which a quantitative analysis was done by HPLC. The analysis showed that the purple-tea extract has GHG of 8.70 percent by mass.

The purple-tea extract was separately prepared twice in the same manner as described above, and the GHG content in the extract was measured by the same method. As a result, the GHG contents were 6.79% and 6.38%, respectively. Therefore, it was verified that the purple-tea extract, prepared according to the method of this invention, has GHG of approximately six to nine percent.

Test Example: Evaluation of the AMPK Activating Effect of the Purple Tea Extract and of the GHG <Method>

Figure 2:
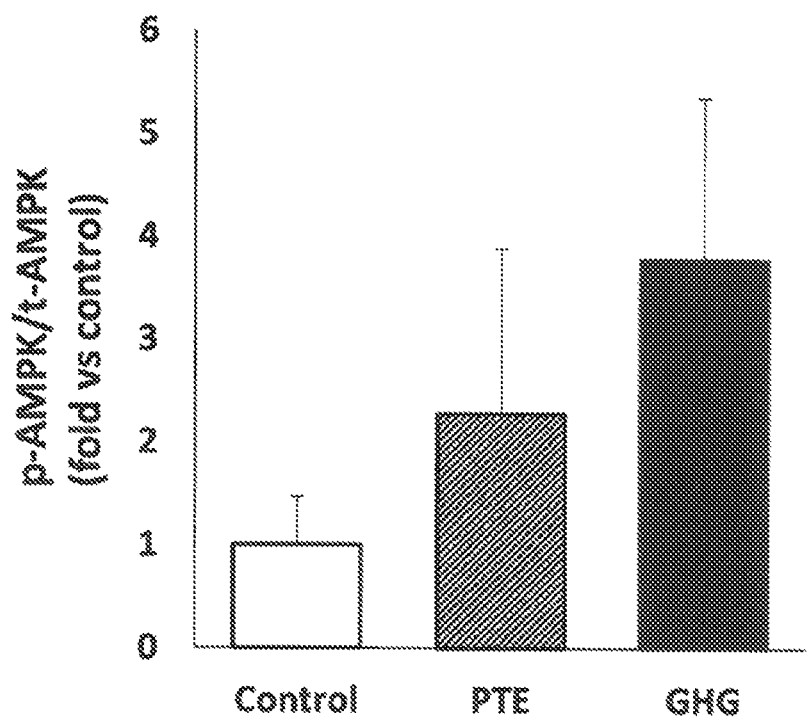
FIG. 2 is a graph showing the evaluation results of the AMPK activating effect of the purple-tea extract and of the GHG.

Mouse-muscle myoblast C2C12 (1×104 pieces/well) was seeded on a plate, and PTE (purple-tea extract (10 μg/ml) and GHG (10 μM) were added to a culture. Every two or three days, the medium was replaced, and candidate ingredients were added. After seven days of incubation, protein was collected. 10% polyacrylamide gel was electrophoresed and transferred to poly vinylidene difluoride film (PVDF). The transferred membrane was blocked by 5% of the BSA/TBS-T, and then such membrane reacted with the first antibody (anti-AMPK or anti-AMPK (phosphor) Abcam) that had been diluted 1,000 times for one hour at room temperature. After the first anti-body reaction was done, the membrane was cleaned with the TBS-T, and then it reacted with the second antibody that had been diluted 2,000 times for one hour at room temperature. Chemiluminescence reaction with an HRP (horseradish peroxidase) was done using a chemiluminescence detection kit (Western blotting substrate plus, ThemoFischer SCIETIFIC). Chemiluminescence was detected using ImageQuant LAS500 (GE Healthcare). By following the densitometric method, based on the image data obtained, the amount of phosphorylated of the AMPK was calculated. FIG. 2 shows the results. In FIG. 2, "p-AMPK" means active AMPK, and "t-AMPK" means total AMPK.

<Result and Effect of the Example>

As shown in FIG. 2, the PTE and GHG showed the AMPK activating effect. Thus, it was recognized that the GHG composition having GHG and the extract of Kenyan purple tea (TRFK306) are useful as the AMPK activating agent.

Examples of the AMPK activating agent of this invention blended with other substances are described below. However, these examples are not limited.

| Blending Example 1: Chewing gums | |
|---|---|
| Sugar | 53.0 wt % |
| Gum base | 20.0 |
| Glucose | 10.0 |
| Starch syrup | 16.0 |

| Blending Example 1: Chewing gums (continued) | |
|---|---|
| Aroma chemical | 0.5 |
| AMPK activating agent | 0.5 |
| | 100.0 wt % |

| Blending Example 2: Gummies | |
|---|---|
| Reduction sugar | 40.0 wt % |
| Granulated sugar | 20.0 |
| Glucose | 20.0 |
| Gelatin | 4.7 |
| Water | 9.68 |
| Kiwi fruit juice | 4.0 |
| Kiwi fruit flavor | 0.6 |
| Pigment | 0.02 |
| AMPK activating agent | 1.0 |
| | 100.0 wt % |

| Blending Example 3: Candies | |
|---|---|
| Sugar | 50.0 wt % |
| Starch syrup | 33.0 |
| Water | 14.4 |
| Organic acid | 2.0 |
| Aroma chemical | 0.2 |
| AMPK activating agent | 0.4 |
| | 100.0 wt % |

| Blending Example 4: Yogurt (Hard type/Soft type) | |
|---|---|
| Milk | 41.5 wt % |
| Powdered skim milk | 5.8 |
| Sugar | 8.0 |
| Agar-agar | 0.15 |
| Gelatin | 0.1 |
| Lactic-acid bacterium | 0.005 |
| AMPK activating agent | 0.4 |
| Aroma chemical | a minute amount |
| Water | the rest |
| | 100.0 wt % |

| Blending Example 5: Soft drinks | |
|---|---|
| Fructose-glucose solution | 30.0 wt % |
| Emulsifying agent | 0.5 |
| AMPK activating agent | 0.05 |
| Aroma chemical | appropriate amount |
| Distilled water | the rest |
| | 100.0 wt % |

| Blending Example 6: Soft capsules | |
| --- | --- |
| Grape seed oil | 87.0 wt % |
| Emulsifying agent | 12.0 |
| AMPK activating agent | 1.0 |
| | 100.0 wt % |

| Blending Example 8: Tablets | |
| --- | --- |
| Lactose | 54.0 wt % |
| Crystalline cellulose | 30.0 |
| Starch-splitting product | 10.0 |
| Glycerin fatty-acid ester | 5.0 |
| AMPK activating aeent | 1.0 |
| | 100.0 wt % |

| Blending Example 8: Oral-granule medicines (drugs and medicines) | |
| --- | --- |
| AMPK activating agent | 1.0 wt % |
| Lactose | 30.0 wt % |
| Corn starch | 60.0 |
| Crystalline cellulose | 8.0 |
| Polyvinylpyrrolidone | 1.0 |
| | 100.0 wt % |

| Blending Example 9: Tablet-shaped sweets (drugs and medicines) | |
| --- | --- |
| Sugar | 76.4 wt % |
| Glucose | 19.0 |
| Sucrose-acid ester | 0.2 |
| AMPK activating agent | 0.5 |
| Distilled water | 3.9 |
| | 100.0 wt % |

| Blending Example 15: Cat foods | |
| --- | --- |
| Corn | 34.0 wt % |
| Wheat flour | 35.0 |
| Oatmeal | 15.0 |
| Beef fat | 8.9 |
| Salt | 1.0 |
| Bonito fish extract | 4.0 |
| AMPK activating agent | 1.0 |
| Taurine | 0.1 |
| Vitamins | 0.5 |
| Minerals | 0.5 |
| | 100.0 wt % |

| Blending Example 16: Dog foods | |
| --- | --- |
| Corn | 30.0 wt % |
| Meats (Chicken) | 15.0 |
| Defatted soybeans | 10.0 |
| Wheat flour | 25.0 |
| Chaff and bran | 5.0 |
| AMPK activating agent | 5.0 |

-continued

| Blending Example 16: Dog foods | |
| --- | --- |
| Animal fat and oil | 8.9 |
| Oligosaccharide | 0.1 |
| Vitamins | 0.5 |
| Minerals | 0.5 |
| | 100.0 wt % |

INDUSTRIAL APPLICABILITY

As descried above, this invention can provide a secure AMPK activating agent with less side effects.

The invention claimed is:

1. A method for activating an AMP activated protein kinase (AMPK) in cells, characterized in comprising the following steps A to C:
   A. a step of extracting 1,2-di-O-calloyl-4,6-O—(S)-hexahydroxydiphenoyl-beta-D-glucose (GHG) by immersing Kenyan purple tea (scientific name: *Camellia sinensis*, variety name: TRFK306) in a polar solvent;
   B. a step of concentrating the extract obtained in step A to obtain a GHG-containing composition; and
   C. a step of administering an effective amount of the GHG-containing composition to the cells, in a subject in need thereof.

2. A method for activating an AMP activated protein kinase (AMPK) in cells, characterized in comprising the following steps A to C:
   A. a step of extracting 1,2-di-O-galloyl-4,6-O—(S)-hexahydroxydiphenoyl-beta-D-glucose (GHG) by immersing a leaf of Kenyan purple tea (scientific name: *Camellia sinensis*, variety name: TRFK306) in hydrous ethanol;
   B. a step of concentrating the extract obtained in step A to obtain a GHG-containing composition; and
   C. a step of administering an effective amount of the GHG-containing composition to the cells, in a subject in need thereof.

3. A method for activating an AMP activated protein kinase (AMPK) in cells, characterized in comprising the following steps A to C:
   A. a step of extracting 1,2-di-O-galloyl-4,6-O—(S)-hexahydroxydiphenoyl-beta-D-glucose (GHG) by immersing Kenyan purple tea (scientific name: *Camellia sinensis*, variety name: TRFK306) in a polar solvent;
   B. a step of freeze-drying or spray-drying the extract obtained in step A to obtain a GHG-containing composition into a powder;
   C. a step of administering an effective amount of the GHG-containing composition to the cells, in a subject in need thereof.

4. A method for activating an AMP activated protein kinase (AMPK) in cells, characterized in comprising the following steps A to C:
   A. a step of extracting 1,2-di-o-galloyl-4,6-O—(S)-hexahydroxydiphenoyl-beta-D-glucose (GHG) by immersing a leaf of Kenyan purple tea (scientific name: *Camellia sinensis*, variety name: TRFK306) in hydrous ethanol;
   B. a step of freeze-drying or spray-drying the extract obtained in step A to obtain a GHG-containing composition into a powder; and C. a step of administering an effective amount of the GHG-containing composition to the cells, in a subject in need thereof.

\* \* \* \* \*